(12) United States Patent
DesNoyer et al.

(10) Patent No.: US 8,034,364 B2
(45) Date of Patent: *Oct. 11, 2011

(54) IMPLANTABLE MEDICAL DEVICE COMPRISING A PRO-HEALING(ESTER-AMIDE)

(75) Inventors: Jessica Reneé DesNoyer, San Jose, CA (US); Mikael Trollsas, San Jose, CA (US); Syed F. A. Hossainy, Fremont, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/775,250

(22) Filed: May 6, 2010

(65) Prior Publication Data

US 2010/0217379 A1    Aug. 26, 2010

Related U.S. Application Data

(63) Continuation of application No. 11/486,553, filed on Jul. 13, 2006, now Pat. No. 7,731,987.

(51) Int. Cl.
*A61F 2/82* (2006.01)
*A61K 31/436* (2006.01)
*A61K 9/00* (2006.01)

(52) U.S. Cl. .......... 424/423; 514/291; 623/1.15
(58) Field of Classification Search .......... 424/423
See application file for complete search history.

(56) References Cited

U.S. PATENT DOCUMENTS

| | | | |
|---|---|---|---|
| 6,503,538 B1 * | 1/2003 | Chu et al. | 424/497 |
| RE40,359 E * | 6/2008 | Katsarava et al. | 424/444 |
| 2005/0033414 A1 * | 2/2005 | Zhang et al. | 623/1.15 |
| 2005/0265960 A1 * | 12/2005 | Pacetti et al. | 424/78.36 |
| 2005/0288481 A1 * | 12/2005 | DesNoyer et al. | 528/310 |

OTHER PUBLICATIONS

Ki, H.C. et al., Polymer 42 (2001) 1849-1861.*
Lewis, Andrew L. et al., Biomaterials, 22 (2001) 99-111.*

* cited by examiner

*Primary Examiner* — David J Blanchard
*Assistant Examiner* — Sarah Alawadi
(74) *Attorney, Agent, or Firm* — Squire, Sanders & Dempsey (US) LLP (57) ABSTRACT

The present invention relates to implantable medical devices, in particular stents, comprising pro-healing poly(ester-amide)s.

42 Claims, 2 Drawing Sheets

IMPLANTABLE MEDICAL DEVICE COMPRISING A PRO-HEALING(ESTER-AMIDE)

CROSS-REFERENCE TO RELATED APPLICATION

This is a continuation application of U.S. application Ser. No. 11/486,553, filed Jul. 13, 2006, now U.S. Pat. No. 7,731,987 the teaching of which is incorporated herein in its entirety by reference.

FIELD

This invention relates to organic chemistry, polymer chemistry, physiology, material science and medical devices.

BACKGROUND

Until the mid-1980s, the accepted treatment for atherosclerosis, i.e., narrowing of the coronary artery(ies) was coronary by-pass surgery. While effective and evolved to a relatively high degree of safety for such an invasive procedure, by-pass surgery still involves potentially serious complications and in the best of cases an extended recovery period.

With the advent of percutaneous tranluminal coronary angioplasty (PTCA) in 1977, the scene changed dramatically. Using catheter techniques originally developed for heart exploration, inflatable balloons were employed to re-open occluded regions in arteries. The procedure was relatively non-invasive, took a very short time compared to by-pass surgery and the recovery time was minimal. However, PTCA brought with it other problems such as vasospasm and elastic recoil of the stretched arterial wall which could undo much of what was accomplished and, in addition, it created a new disease, restenosis, the re-clogging of the treated artery due to neointimal hyperplasia.

The next improvement, advanced in the mid-1980s was the use of a stent to maintain the luminal diameter after PTCA. This for all intents and purposes put an end to vasospasm and elastic recoil but did not entirely resolve the issue of restenosis. That is, prior to the introduction of stents, restenosis occurred in from 30-50% of patients undergoing PTCA. Stenting reduced this to about 15-20%, much improved but still more than desirable.

In 2003, drug-eluting stents or DESs were introduced. The drugs initially employed with the DES were cytostatic compounds, that is, compounds that curtailed the proliferation of cells that resulted in restenosis. The occurrence of restenosis was thereby reduced to about 5-7%, a relatively acceptable figure. However, the use of DESs engendered a new problem, late stent thrombosis, the forming of blood clots long after the stent was in place. It was hypothesized that the formation of blood clots was most likely due to delayed healing, a side-effect of the use of cytostatic drugs.

What is needed is an implantable medical device that includes a pro-healing influence to counter the delayed healing due to the eluting drugs. While this would be particularly useful with regard to coronary stents, it would also provide substantial benefit to any manner of implantable medical device. For instance, it has been stated that the occurrence of restenosis in the case of lower extremity percutaneous angioplasty is particularly unacceptable (Paul S. Teirstein, *Circulation*, 2000, 102:2674) and it would be expected that this situation would also be amenable to the effects of stents having pro-healing properties. The present invention provides such implantable medical devices.

SUMMARY

Thus, in one aspect, the current invention relates to an implantable medical device, comprising:
a device body;
an optional primer layer disposed over the device body;
a drug reservoir layer disposed over the device body or the primer layer if opted, wherein the drug reservoir layer comprises one or more therapeutic agents;
an optional rate-controlling layer disposed over at least a portion of the drug reservoir layer, if opted; and,
an optional top-coat layer disposed as an outermost layer over the device body, the primer layer, if opted, the drug reservoir layer, if opted, or the rate-limiting layer, if opted, wherein:
at least one of the layers comprises a poly(ester-amide) having the formula:

wherein:
m is an integer from 0 to about 200;
p is an integer from 0 to about 200;
n is an integer from 0 to about 200;
r is an integer from 1 to about 3000;
$M_w$ is from about 10,000 Da to about 1,000,000 Da;
s is a number from 0 to 1, inclusive;
t is a number from 0 to 1, inclusive;
v is a number from 0 to 1, inclusive; wherein s+t+v=1;
X has the chemical structure:

Y has the chemical structure:

Z has the chemical structure:

wherein:
  $R_1$, $R_{1'}$ and $R_4$ are independently selected from the group consisting of (1C-12C)alkyl and (2C-12C)alkenyl;
  $R_2$, $R_{2'}$, $R_{2''}$ and $R_{2'''}$ are independently selected from the group consisting of hydrogen and (1C-4C)alkyl, wherein:
    the alkyl group is optionally substituted with a moiety selected from the group consisting of —OH, —O(1C-4C)alkyl, —SH, —S(1C-4C)alkyl, —SeH, —COR$_6$, —NHC(NH)NH$_2$, imidazol-2-yl, imidazole-5-yl, indol-3-yl, phenyl, 4-hydroxyphenyl and 4-[(1C-4C)alkylO]phenyl, wherein:

R$_6$ is selected from the group consisting of —OH, —O(1C-4C)alkyl, —NH$_2$, —NH(1C-4C)alkyl, —N(1C-4C)alkyl$_1$(1C-4C)alkyl$_2$, a stable nitroxide, —O(CH)$_2$OP(=O)(O$^-$)OCH$_2$CH$_2$N$^+$(CH$_3$)$_3$, —O(CH$_2$CH$_2$O)$_q$CH$_2$CH$_2$OR$_7$ and where:

R$_7$ is selected from the group consisting of hydrogen, (1C-4C)alkyl, —C(O)CH=CH$_2$ and —C(O)C(CH$_3$)=CH$_2$;

or one or more of R$_2$, R$_{2'}$, R$_{2''}$ and R$_{2'''}$ may form a bridge between the carbon to which it is attached and the adjacent nitrogen, the bridge comprising —CH$_2$CH$_2$CH$_2$—;

R$_3$ is selected from the group consisting of (1C-12C)alkyl and (2C-12C)alkenyl, (3C-8C)cycloalkyl and —(CH$_2$CH$_2$O)$_q$CH$_2$CH$_2$—;

R$_5$ is selected from the group consisting of —CH(COR$_6$)CH$_2$S—, —CH(COR$_6$)CH$_2$O—, —CH(COR$_6$)(CH$_2$)$_4$NH—, —(CH$_2$)$_4$CH(COR$_6$)NH—, —CH(COR$_6$)CH(CH$_3$)O—, q is an integer from 1 to 600, inclusive.

In an aspect of this invention, M$_w$ is from about 20,000 Da to about 500,000 Da.

In an aspect of this invention, at least an outermost layer comprises the poly(ester-amide).

In an aspect of this invention, the outermost layer is a topcoat layer.

In an aspect of this invention R$_1$ is selected from the group consisting of —(CH$_2$)$_4$—, —(CH$_2$)$_8$—, and —CH$_2$CH=CHCH$_2$— and R$_{1'}$ and R$_4$ are selected from the group consisting of —(CH$_2$)$_4$— and —(CH$_2$)$_8$—.

In an aspect of this invention, R$_2$ is —CH$_2$CH(CH$_3$)$_2$.

In an aspect of this invention, R$_3$ is —(CH$_2$)$_6$— and R$_{3'}$ is

In an aspect of this invention R$_5$ is —(CH$_2$)$_4$COR$_6$NH—, wherein R$_6$ is selected from the group consisting of —O(CH)$_2$ OP(=O)(O$^-$)OCH$_2$CH$_2$N$^+$(CH$_3$)$_3$ and —O(CH$_2$CH$_2$O)$_q$ CH$_2$CH$_2$OR$_7$, wherein R$_7$ is selected from the group consisting of hydrogen, (1C-4C)alkyl, —C(O)CH=CH$_2$ and —C(O)C(CH$_3$)=CH$_2$.

In an aspect of this invention, p=0.

In an aspect of this invention, when p=0, R$_1$ and R$_4$ are independently selected from the group consisting of —(CH$_2$)$_4$— and —(CH$_2$)$_8$—.

In an aspect of this invention, when p=0, R$_2$ and R$_{2'}$ are independently selected from the group consisting of —CH$_3$, —CH$_2$CH$_2$NHC(NH)NH$_2$, —CH$_2$CONH$_2$, —CH$_2$COOH, —CH$_2$SH, —CH$_2$CH$_2$COOH, —CH$_2$CH$_2$CONH$_2$, —CH$_2$NH$_2$, —CH(CH$_3$)CH$_2$CH$_3$, —CH$_2$CH(CH$_3$)$_2$, —(CH$_2$)$_4$NH$_2$, (CH$_2$)$_2$SCH$_3$,

CH$_2$OH, —CH(CH$_3$)OH,

—CH(CH$_3$)$_2$ and —CH$_2$CH$_2$CH$_2$—, wherein the second carbon is covalently bonded to the nitrogen adjacent to the carbon to which R$_2$ is bonded.

In an aspect of this invention, when p=0, R$_3$ is selected from the group consisting of —(CH$_2$)$_3$—, —(CH$_2$)$_6$— and —(CH$_2$CH$_2$O)$_q$CH$_2$CH$_2$—, wherein q is an integer from 1 to 10, inclusive.

In an aspect of this invention, when p=0, R$_5$ is —(CH$_2$)$_4$CH(COR$_6$)NH—, wherein R$_6$ is selected from the group consisting of a stable nitroxide, —O(CH$_2$)$_2$OP(=O)(O$^-$)OCH$_2$CH$_2$N$^+$(CH$_3$)$_3$ and —O(CH$_2$CH$_2$O)$_q$CH$_2$CH$_2$OR$_7$, wherein R$_7$ is selected from the group consisting of hydrogen, (1C-4C)alkyl, —C(O)CH=CH$_2$ and —C(O)C(CH$_3$)=CH$_2$.

In an aspect of this invention, when p=0, R$_2$ and R$_{2'}$ are identical.

In an aspect of this invention, when p=0, R$_2$ and R$_{2'}$ are —CH$_2$CH(CH$_3$)$_2$.

In an aspect of this invention, when p=0, the stable nitroxide is selected from the group consisting of In an aspect of this invention, when p=0, the stable nitroxide is In an aspect of this invention, when p=0, R$_6$ is In an aspect of this invention, p=0 and n=0.

In an aspect of this invention, when p=0 and n=0, R$_2$ and R$_{2'}$ are selected from the group consisting of —CH$_3$, —H$_2$CH$_2$NHC(NH)NH$_2$, —CH$_2$CONH$_2$, —CH$_2$COOH, —CH$_2$SH, —CH$_2$CH$_2$COOH, —CH$_2$CH$_2$CONH$_2$, —CH$_2$NH$_2$, —CH(CH$_3$)CH$_2$CH$_3$. —CH$_2$CH(CH$_3$)$_2$, —(CH$_2$)$_4$NH$_2$, (CH$_2$)$_2$SCH$_3$,

CH$_2$OH, —CH(CH$_3$)OH,

CH(CH$_3$)$_2$ and —CH$_2$CH$_2$CH$_2$—, wherein the second carbon is covalently bonded to the nitrogen adjacent to the carbon to which R$_2$ is bonded.

In an aspect of this invention, when p=0 and n=0, R$_1$ is selected from the group consisting of —(CH$_2$)$_4$—, —(CH$_2$)$_8$— and —CH$_2$CH=CHCH$_2$—.

In an aspect of this invention, when p=0 and n=0, R$_2$ and R$_{2'}$ are the same.

In an aspect of this invention, when p=0 and n=0, R$_2$ and R$_{2'}$ are CH$_2$CH(CH$_3$)$_2$.

In an aspect of this invention, when p=0 and n=0, R$_3$ is selected from the group consisting of (3C-8C) alkyl, —(CH$_2$CH$_2$O)$_q$CH$_2$CH$_2$—, wherein q is an integer from 1 to 10, inclusive, In an aspect of this invention, when p=0 and n=0, q is 2.

In an aspect of this invention, when p=0 and n=0, R$_3$ is selected from the group consisting of —(CH$_2$)$_3$— and —(CH$_2$)$_6$—.

In an aspect of this invention, when p=0 and n=0, R$_3$ is

In an aspect of this invention, when p=0 and n=0, $R_2$ and $R_{2'}$ are benzyl.

In an aspect of this invention, the implantable medical device further comprises a drug reservoir layer and a rate-controlling layer, wherein the rate-controlling layer comprises a polymer selected from the group consisting of poly (l-lactide), poly(D-lactide), poly(D,L-lactide), poly(meso-lactide), poly(L-lactide-co-glycolide), poly(D-lactide-co-glycolide), poly(D,L-lactide-co-glycolide), poly(meso-lactide-co-glycolide) and an combination thereof.

In an aspect of this invention, the rate-controlling layer comprises poly(D,L-lactide).

In an aspect of this invention, the implantable medical device further comprises a drug reservoir layer, wherein the drug reservoir layer comprises one or more drugs disposed neat over the primer layer.

In an aspect of this invention, the implantable medical device further comprises a drug reservoir layer, wherein the drug reservoir layer comprises one or more polymers.

In an aspect of this invention, the therapeutic agent is everolimus.

In an aspect of this invention, the drug reservoir layer polymer is selected from the group consisting of poly(vinylidene fluoride) and poly(vinylidene fluoride-co-hexafluoropropylene).

In an aspect of this invention, the implantable medical device further comprises a primer layer, wherein the primer layer comprises poly(n-butyl methacrylate).

An aspect of this invention is a stent, comprising a poly(n-butyl methacrylate) primer, a poly(vinylidene fluoride-co-hexafluoropropylene) drug reservoir layer comprising everolimus and a topcoat layer comprising a poly(ester-amide).

In an aspect of this invention, the poly(ester-amide) in the aspect immediately above is selected from the group consisting of PEA-TEMPO and PEA-BZ.

In an aspect of this invention, one or more of $R_2$, $R_{2'}$, $R_{2''}$, $R_{2'''}$ and $R_5$ comprises a pendant —$COR_6$ group wherein each $R_6$ is independently selected from the group consisting of a stable nitroxide entity, benzylO—, —$O(CH_2)_2OP(=O)(O)CH_2CH_2N^+(CH_3)_3$ and —$O(CH_2CH_2O)_qCH_2CH_2OR_7$.

In an aspect of this invention, an outermost layer comprises the poly(ester-amide).

In an aspect of this invention, the outermost layer is a topcoat layer.

In an aspect of this invention, in the aspect immediately above, the stable nitroxide is selected from the group consisting of In an aspect of this invention, in the aspect two paragraphs above, q is 1-10, inclusive.

In an aspect of this invention, in the aspect three paragraphs above, q is 300-600, inclusive.

In an aspect of this invention, in the aspect four paragraphs above, $R_6$ is —$O(CH_2)_2OP(=O)(O)CH_2CH_2N^+(CH_3)_3$.

In an aspect of this invention, the implantable medical device is a stent.

DETAILED DESCRIPTION

Use of the singular herein includes the plural and visa versa unless expressly stated to be otherwise. That is, "a" and "the" refer to one or more of whatever the word modifies. For example, "a therapeutic agent" includes one such agent, two such agents, etc. Likewise, "the layer" may refer to one, two or more layers and "the polymer" may mean one polymer or a plurality of polymers. By the same token, words such as, without limitation, "layers" and "polymers" would refer to one layer or polymer as well as to a plurality of layers or polymers unless, again, it is expressly stated or obvious from the context that such is not intended.

As used herein, any words of approximation such as without limitation, "about," "essentially," "substantially" and the like mean that the element so modified need not be exactly what is described but can vary from the description by as much as ±15% without exceeding the scope of this invention.

As used herein, "if opted" means that the item being discussed is optional and if the option is exercised the condition that follows the phrase will pertain.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, PFO closure devices, arterial closure devices, artificial heart valves and cerebrospinal fluid shunts.

An implantable medical device specifically designed and intended solely for the localized delivery of a therapeutic agent is within the scope of this invention.

As used herein, "device body" refers to a fully formed implantable medical with an outer surface to which no coating or layer of material different from that of which the device itself is manufactured has been applied. By "outer surface" is meant any surface however spatially oriented that is in contact with bodily tissue or fluids. A common example of a "device body" is a BMS, i.e., a bare metal stent, which, as the name implies, is a fully-formed usable stent that has not been coated with a layer of any material different from the metal of which it is made on any surface that is in contact with bodily tissue or fluids. Of course, device body refers not only to BMSs but also to any uncoated device regardless of what it is made of.

Implantable medical devices made of virtually any material, i.e., materials presently known to be useful for the manufacture of implantable medical devices and materials that may be found to be so in the future, may be used with a coating of this invention. For example, without limitation, an implantable medical device useful with this invention may be made of one or more biocompatible metals or alloys thereof including, but not limited to, cobalt-chromium alloy (ELGILOY, L-605), cobalt-nickel alloy (MP-35N), 316L stainless steel, high nitrogen stainless steel, e.g., BIODUR 108, nickel-titanium alloy (NITINOL), tantalum, platinum, platinum-iridium alloy, gold and combinations thereof.

Implantable medical devices may also be made of polymers that are biocompatible and biostable or biodegradable, the latter term including bioabsorbable and bioerodable.

As used herein, "biocompatible" refers to a polymer that both in its intact, as synthesized state and in its decomposed state, its degradation products, are not toxic, or at least are minimally toxic, to living tissue; does not, or at least minimally and reparably, injure(s) living tissue; and/or does not, or at least minimally and controllably, cause(s) an immunological reaction in living tissue.

Among useful biocompatible, relatively biostable polymers are, without limitation, polyacrylates, polymethacrylates, polyureas, polyurethanes, polyolefins, polyvinylhalides, polyvinylidenehalides, polyvinylethers, polyvinylaromatics, polyvinylesters, polyacrylonitriles, alkyd resins, polysiloxanes and epoxy resins.

Biocompatible, biodegradable polymers include naturally-occurring polymers such as, without limitation, collagen, chitosan, alginate, fibrin, fibrinogen, cellulosics, starches, dextran, dextrin, hyaluronic acid, heparin, glycosaminoglycans, polysaccharides and elastin.

One or more synthetic or semi-synthetic biocompatible, biodegradable polymers may also be used to fabricate an implantable medical device useful with this invention. As used herein, a synthetic polymer refers to one that is created wholly in the laboratory while a semi-synthetic polymer refers to a naturally-occurring polymer than has been chemically modified in the laboratory. Examples of synthetic polymers include, without limitation, polyphosphazines, polyphosphoesters, polyphosphoester urethane, polyhydroxyacids, polyhydroxyalkanoates, polyanhydrides, polyesters, polyorthoesters, polycarbonates, polyiminocarbonates, polyamino acids, polyoxymethylenes, poly(esteramides) and polyimides.

Blends and copolymers of the above polymers may also be used and are within the scope of this invention. Based on the disclosures herein, those skilled in the art will recognize those implantable medical devices and those materials from which they may be fabricated that will be useful with the coatings of this invention.

At present, preferred implantable medical devices for use with the coatings of this invention are stents.

A stent refers generally to any device used to hold tissue in place in a patient's body. Particularly useful stents, however, are those used for the maintenance of the patency of a vessel in a patient's body when the vessel is narrowed or closed due to diseases or disorders including, without limitation, tumors (in, for example, bile ducts, the esophagus, the trachea/bronchi, etc.), benign pancreatic disease, coronary artery disease, carotid artery disease, renal artery disease and peripheral arterial disease such as atherosclerosis, restenosis and vulnerable plaque. Vulnerable plaque (VP) refers to a fatty build-up in an artery thought to be caused by inflammation. The VP is covered by a thin fibrous cap that can rupture leading to blood clot formation. A stent can be used to strengthen the wall of the vessel in the vicinity of the VP and act as a shield against such rupture. A stent can be used in, without limitation, neuro, carotid, coronary, pulmonary, aortic, renal, biliary, iliac, femoral and popliteal as well as other peripheral vasculatures. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

In addition to the above uses, stents may also be employed for the localized delivery of therapeutic agents to specific treatment sites in a patient's body. In fact, therapeutic agent delivery may be the sole purpose of the stent or the stent may be primarily intended for another use such as those discussed above with drug delivery providing an ancillary benefit.

A stent used for patency maintenance is usually delivered to the target site in a compressed state and then expanded to fit the vessel into which it has been inserted. Once at a target location, a stent may be self-expandable or balloon expandable. In any event, due to the expansion of the stent, any coating thereon must be flexible and capable of elongation.

As used herein, "optional" means that the element modified by the term may or may not be present. For example, without limitation, a device body (db) that has coated on it an "optional" primer layer (pl), an "optional" drug reservoir layer (dr), an "optional" rate-controlling layer (rc) and a top-coat layer (tc) (which it should be noted is not optional herein) refers, without limitation, to any of the following devices: db+tc, db+dr+tc, db+dr+rc+tc, db+pl+tc, db+pl+dr+tc and db+pl+dr+rc+tc.

As used herein, a "primer layer" refers to a coating consisting of a polymer or blend of polymers that exhibit good adhesion characteristics with regard to the material of which the device body is manufactured and good adhesion characteristic with regard to whatever material is to be coated on the device body. Thus, a primer layer serves as an intermediary layer between a device body and materials to be affixed to the device body and is, therefore, applied directly to the device body. Examples without limitation, of primers include silanes, titanates, zirconates, silicates, parylene, vinyl alcohol copolymers, acrylic acid copolymers, methacrylic acid copolymers, polyethyleneamine, polyallylamine, acrylate and methacrylate polymers with poly(n-butyl methacrylate) being a presently preferred primer.

As use herein, a material that is described as a layer "disposed over" an indicated substrate, e.g., without limitation, a device body or another layer, refers to a relatively thin coating of the material applied, preferably at present, directly to essentially the entire exposed surface of the indicated substrate. By "exposed surface" is meant that surface of the substrate that, in use, would be in contact with bodily tissues or fluids. "Disposed over" may, however, also refer to the application of the thin layer of material to an intervening layer that has been applied to the substrate, wherein the material is applied in such a manner that, were the intervening layer not present, the material would cover substantially the entire exposed surface of the substrate.

As used herein, "drug reservoir layer" refers either to a layer of one or more therapeutic agents applied neat or to a layer of polymer or blend of polymers that has dispersed within its three-dimensional structure one or more therapeutic agents. A polymeric drug reservoir layer is designed such that, by one mechanism or another, e.g., without limitation, by elution or as the result of biodegradation of the polymer, the therapeutic substance is released from the layer into the surrounding environment.

As used herein, "therapeutic agent" refers to any substance that, when administered in a therapeutically effective amount to a patient suffering from a disease, has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to retrogress; or, (4) alleviating one or more symptoms of the disease. As used herein, a therapeutic agent also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease in the first place; (2) maintaining a disease at a retrogressed level once such level has been achieved by a therapeutically effective amount of a substance, which may be the same as or different from the substance used in a prophylactically effective amount; or, (3) preventing or delaying recurrence of the disease after a course of treatment with a therapeutically effective amount of a substance, which may be the same as or different from the substance used in a prophylactically effective amount, has concluded.

As used herein, the terms "drug" and "therapeutic agent" are used interchangeably.

As used herein, "rate-controlling layer" refers to a polymeric layer that is applied over a drug reservoir layer to modify the rate of release into the environment of the therapeutic agents from the drug reservoir layer. A rate-controlling layer may be used simply to "tune" the rate of release of a therapeutic agent to exactly that desired by the practitioner or it may be a necessary adjunct to the construct because the polymer or blend of polymers with which the therapeutic agent is compatible with regard to coating as a drug reservoir layer may be too permeable to the therapeutic substance resulting in too rapid release and delivery of the therapeutic substance into a patient's body. A non-limiting example is an everolimus drug reservoir layer comprising PEA-TEMPO (a poly(ester-amide) to which 2,2,6,6-tetramethyl-4-aminopiperidineoxyl has been covalently appended). While PEA-TEMPO has very desirable in vivo properties, it is quite permeable to everolimus. Thus, sustained release (i.e., release of a therapeutically effective amount of a drug over an extended period of time which may be a few days, a few months, or even longer) of everolimus from a poly(ester-amide) polymer matrix is difficult and in some cases impossible to achieve. To ameliorate this situation, a rate-controlling polymer or blend of polymers through which the everolimus must pass can be applied over the more PEA-TEMPO layer. The reduced permeability of everolimus through the rate-controlling layer may be due, without limitation, to inherent characteristics of the polymer and its interaction with a given therapeutic agent or it may be due to such factors as cross-linking of the rate-controlling polymer.

A poly(ester-amide) refers to a polymer that has in its backbone structure both ester and amide bonds. For example, the following formula represents a poly(ester-amide) of this invention:

X, Y and Z refer to the constitutional units, i.e., the repeating units, of the polymer. For example, in the polymer is the X constitutional unit and is the Z constitutional unit, Y being absent, i.e., p is 0. The constitution units themselves can be the product of the reactions of other compounds. For example, without limitation, the X constitutional unit above may comprises the reaction of an amino acid, with a diol, HO—($R_3$)—OH, to give a diamino ester, which is then reacted with a diacid, to give the constitutional unit. The amine group, the carboxylic acid group or the hydroxyl group may be "activated," i.e., rendered more chemically reactive, to facilitate the reactions if desired; such activating techniques are well-known in the art and the use of any such techniques is within the scope of this invention. A non-limiting example of the synthesis of an exemplary but not limiting X constitution unit having the above general structure is the reaction of 1,6-hexane diol with l-leucine to give the diamino diester, which is then reacted with sebacic acid to give X. Constitutional unit Y can be obtained by the same reactions as those affording X but using one or more different reactants such that the resulting constitutional units X and Y are chemically different or Y may result from the reaction of a diacid with a tri-functional amino acid wherein two of the functional groups are capable of reacting with the diacid. As example of the foregoing would be the reaction of sebacic acid or an activated derivative thereof, with l-lysine, i.e., 2,6-diaminohexanoic acid.

With regard to the synthesis of the poly(ester-amide)s of this invention, it will be noted that no specific reactions or reaction conditions are exemplified herein. This is because the reactions and reaction conditions both for the preparation of constitutional units and for the preparation of the final poly(ester-amide) comprise standard organic and polymer chemistry well-known to those of ordinary skill in the art and, therefore, those skilled artisans will be able to prepare any of the compounds herein without undue experimentation based on the disclosures herein.

As for the amino acids selected for the preparation of poly(ester-amide)s of this invention, any may be use; however, at present it is preferred that the amino acids be selected from the group commonly known as the standard amino acids or sometimes the proteinogenic amino acids because they are encoded by the normal genetic code. There currently are 20 standard amino acids: alanine, arginine, asparagine, aspartic acid, cysteine, glutamic acid, glutamine, glycine, histidine, isoleucine, leucine, lysine, methionine, phenyl alanine, proline, serine, threonine, tryptophan, tyrosine and valine. Relatively recently selenoadenine has been found to be incorporated into a number of proteins and is included with the above as a useful amino acid for the purposes of this invention. In naturally-occurring biological proteins, these amino acids exist primarily as l-enantiomers but for the purposes of this invention they may be used as their l- or d-enantiomers or as racemic mixtures.

In the above formula, m, p and n are integers that represent the average number of constitutional units X, Y and Z in an uninterrupted string or, if there is more than on, block; i.e., the number of X units before a Y unit is encountered, etc. The integers m, p and n can be any number, including 0; when two of m, p and n are 0, the resulting poly(ester-amide) is a homopolymer.

In the above formula, r represents the total number of X, Y and Z units in the polymer and can be any integer from 1 to about 2500, with the proviso that the combination of m, p, n and r should provide a poly(ester-amide) that has a molecular weight within the range discussed below.

In the above formula, $M_n$ represents the number average molecular weight of a poly(ester-amide) of this invention. Again, while any molecular weight that results in a polymer that has the requisite properties to useful with the implantable medical devices of this invention, properties that are well-known to those skilled in the art, is within the scope of this invention, at present the number average molecular weight of a poly(ester-amide) of this invention is from about 10,000 Da (Daltons) to about 1,000,000 Da, preferably at present from about 20,000 Da to about 500,000 Da.

Also in the above formula, s, t and v represent the mole fraction of each of the constitutional units. Each of s, t and v is a number between 0 and 1, inclusive with s+t+v=1. It is understood that the mole fraction and the number of constitutional units are related and the designation of one will affect the other.

As noted s, t and v may each be 0, 1 or any fraction between. There are, however, certain provisos: (1) if an additional prohealing entity is present on one of the constitutional units, that constitutional unit must be at least 0.02 mol fraction of the polymer; and (2) m and p can both be 0 only if $R_5$ is selected from the group consisting of —CH(COR$_6$)CH$_2$S—, —CH(C(O)R$_6$CH$_2$O—, —CH(COR$_6$)CH(CH$_3$)O— and because otherwise the resulting homopolymer would not be a poly(ester-amide). Other than the preceding provisos, any values of s, t and v that provides a polymer having desirable properties for the intended use, e.g., as a drug reservoir layer, a rate-controlling layer, etc., and those skilled in the art will be readily able to make such variations and determine if the resulting polymer as the requisite properties based on the disclosures herein without undue experimentation.

The polymers of this invention may be regular alternating polymers, random alternating polymers, regular block polymers, random block polymers or purely random polymers unless expressly noted otherwise. A regular alternating polymer has the general structure: . . . x-y-z-x-y-z-x-y-z- . . . . A random alternating polymer has the general structure: . . . x-y-x-z-x-y-z-y-z-x-y- . . . , it being understood that the exact juxtaposition of the various constitution units may vary. A regular block polymer has the general structure: . . . x-x-x-y-y-y-z-z-z-x-x-x . . . , while a random block polymer has the general structure: . . . x-x-x-z-z-x-x-y-y-y-z-z-z-x-x-z-z-z- . . . . Similarly to the situation above regarding regular and alternating polymers, the juxtaposition of blocks, the number of constitutional units in each block and the number of blocks in block polymers of this invention are not in any manner limited by the preceding illustrative generic structures.

Constitutional unit Z, on the other hand, is the result of the reaction of a diacid with a tri-functional amino acid wherein two of the functional groups are capable of reacting with the diacid. As example would be the reaction of sebacic acid or an activated derivative thereof, with l-lysine, 2,6-diaminohexanoic acid, the two amino groups being capable of reacting with the diacid carboxyl groups to form amides.

The poly(ester-amides) of this invention may be used as is, that is, as the product of amino acids, diacids and diols as described above because it has been found that the poly(ester-amide)s of this invention exhibit pro-healing properties in their own right. It is an aspect of this invention, however, that a poly(ester-amide) of this invention may be further modified by the attachment of an additional pro-healing moiety to an appropriate pendant group attached to the polymer backbone. By pro-healing moiety is meant a substituent group that is biocompatible and that aids in the amelioration of inflammation and/or in the endothelialization of the implantable medical device. Such substituent groups include, without limitation, stable nitroxides; phosphorylcholine, $-O(CH)_2OP(=O)(O^-)OCH_2CH_2N^+(CH_3)_3$, nitric oxide donors, nitric oxide generating catalysts that utilize nitrosothiols, oligomers of ethylene glycol or ethylene oxide; poly(ethylene glycol) and end-group modified derivatives thereof, i.e., $-O(CH_2CH_2O)_qCH_2CH_2OR_7$, wherein $R_7$ is selected from the group consisting of hydrogen, (1C-4C)alkyl, $-C(O)CH=CH_2$, $-C(O)C(CH_3)=CH_2$ and phosphorylcholine. If $R_7$ comprises a double bond, double bonds on different polymer chains may be reacted with one another using UV light or a free radical initiator to give a crosslinked poly(ester-amide).

As used herein, "alkyl" refers to a straight or branched chain fully saturated (no double or triple bonds) hydrocarbon (carbon and hydrogen only) group. The alkyl groups of this invention may range from $C_1$ to $C_{12}$, preferably $C_2$ to $C_{10}$ and currently most preferably $C_3$ to $C_8$. Examples of alkyl groups include, but are not limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, and cyclohexyl. In addition, as used herein "alkyl" includes "alkylene" groups, which refer to straight or branched fully saturated hydrocarbon groups having two rather than one open valences for bonding to other groups. Examples of alkylene groups include, but are not limited to methylene, $-CH_2-$, ethylene, $-CH_2CH_2-$, propylene, $-CH_2CH_2CH_2-$, n-butylene, $-CH_2CH_2CH_2CH_2-$, sec-butylene, $-CH_2CH_2CH(CH_3)-$ and the like.

As used herein, "mC to nC," wherein m and n are integers refers to the number of possible carbon atoms in the indicated group. That is, the group can contain from "m" to "n", inclusive, carbon atoms. An alkyl group of this invention may comprise from 1 to 12 carbon atoms, that is, m may be 1 and n may be 12. Of course, a particular alkyl group may be more limited, for instance without limitation, to 3 to 8 carbon atoms, in which case it would be designate as a (3C-8C)alkyl group. The numbers are inclusive and incorporate all straight or branched chain structures having the indicated number of carbon atoms. For example without limitation, a "$C_1$ to $C_4$ alkyl" group refers to all alkyl groups having from 1 to 4 carbons, that is, $CH_3-$, $CH_3CH_2-$, $CH_3CH_2CH_2-$, $CH_3CH(CH_3)-$, $CH_3CH_2CH_2CH_2-$, $CH_3CH_2CH(CH_3)-$ and $(CH_3)_3CH-$.

As use herein, "cycloalkyl" refers to an alkyl group in which the end carbon atoms of the alkyl chain are covalently bonded to one another. In cycloalkyl groups, the numbers "m" to "n" refer to the number of carbon atoms in the ring so formed. Thus for instance, a (3C-8C)cycloalkyl group refers to a three, four, five, six, seven or eight member ring, that is, cyclopropane, cyclobutane, cyclopentane, cyclohexane, cycloheptane and cyclooctane.

As used herein, "bicycloalkyl" refers to two cycloalkyl groups bonded together by a single covalent bond. An example, without limitation, of a bicycloalkyl group is bicyclohexane, As used herein, "benzyl" refers to a phenylmethylene, group.

As used herein, "alkenyl" refers to an alkyl group that contains in the straight or branched hydrocarbon chain one or more double bonds.

If a group of this invention is described as being "optionally substituted" it means that that group may be unsubstituted or substituted with one or more of the indicated substituents.

Standard shorthand designations well-known to those skilled in the art are used throughout this application. Thus the intended structure will easily be recognizable to those skilled in the art based on the required valency of any particular atom with the understanding that all necessary hydrogen atoms are provided. For example, $-COR$, because carbon is tetravalent, must refer to the structure as that is the only way the carbon can be tetravalent without the addition of unshown hydrogen or other atoms. Similarly, $-O(CH)_2OP(=O)(O^-)OCH_2CH_2N^+(CH_3)_3$ refers to the structure Likewise, it is understood by those skilled in the chemical arts that so-called stick structure, exemplified by represents the structure that is, each terminus is capped with a $CH_3$ group and the apex of each angle is a carbon atom with the requisite number of hydrogens attached.

The designation of two or more alkyl moieties as $alkyl_1$, $alkyl_2$, etc., means that the alkyl groups may be the same or different.

As used herein, a "stable nitroxide" refers to an isolatable paramagnetic organic compound having the generic structure RR'N—O wherein R and R' may be aliphatic or may join to form a ring which may be acyclic or aromatic. In addition, for the purposes of this invention, the stable nitroxide must also contain at least one functional group through which the nitroxide may be covalently bonded to a poly(ester-amide) of this invention. For example, without limitation, 4-amino-2,2,6,6-tetramethylpiperidine-1-oxyl can be reacted with a pendant carboxylic acid group of, without limitation, lysine that comprises the backbone of a poly(ester-amide) of this invention, to form an amide. Other such functional groups that will afford covalently bonded stable nitroxides will be evident to those skilled in the art based on the disclosures herein and are within the scope of this invention.

As used herein, to dispose a layer of "neat" therapeutic agent simply means that the therapeutic agent, once it is has been applied to a surface and any solvent used during the application has been allowed to evaporate, the therapeutic agent is the only constituent of the layer, i.e., there is essentially no solvent, no polymers, no excipients or any other material in the layer other than the therapeutic agent in essentially the same purity as it had before being applied to the device.

Figure 1:
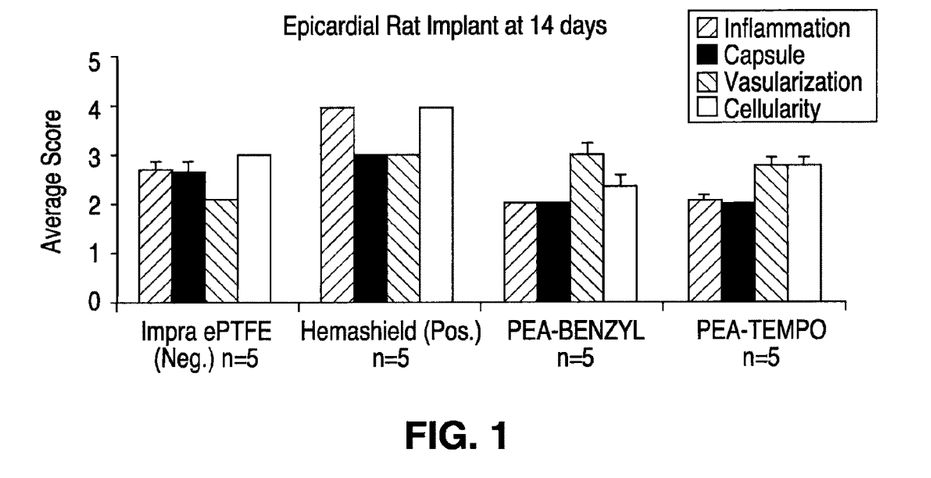
FIG. 1 graphically depicts the inflammatory and cellular response elicited by Impra® graft material, Hemashield® graft material, PEA-TEMPO and PEA-BZ at 14 days post-implantation in rat epicardial tissue.
Figure 2:
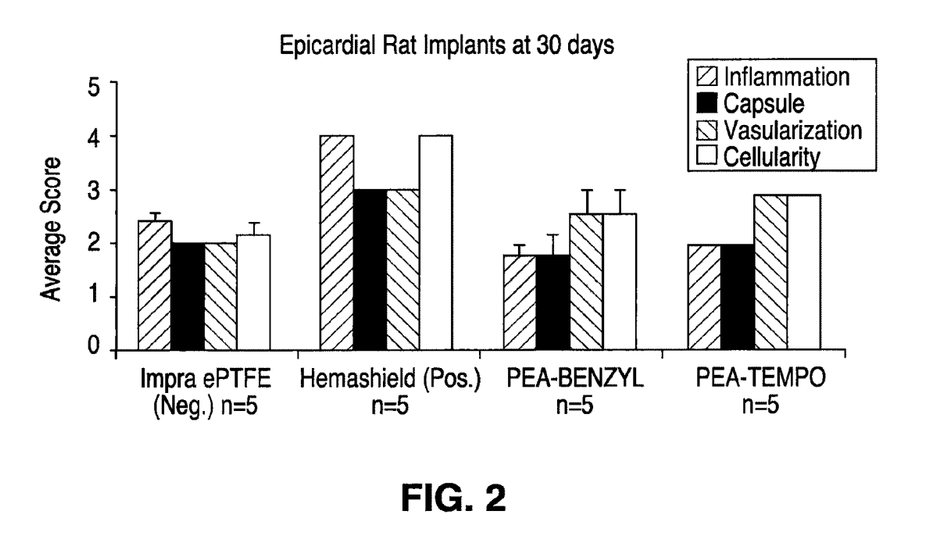
FIG. 2 graphically depicts the inflammatory and cellular response elicited by Impra® graft material, Hemashield® graft material, PEA-TEMPO and PEA-BZ at 30 days post-implantation in rat epicardial tissue.

The poly(ester-amides) of this invention have been found to have beneficial pro-healing properties in vivo, in particular with regard to inflammation and neovascularization. For example, without limitation, a comparison of the inflammatory responses elicited in vivo by test discs made of two poly(ester-amides) of this invention, co-poly-{[N,N'-sebacoyl-bis-(L-leucine)-1,6-hexylenediester]-[N,N'-sebacoyl-L-lysine benzyl ester]} (PEA-BZ) and co-poly-{[N,N'-sebacoyl-bis-(L-leucine)-1,6-hexylene diester]-[N,N'-sebacoyl-L-lysine 4-amino-2,2,6,6-tetramethylpiperidine-1-oxyl amide]} (PEA-TEMPO), with that caused by test discs made of two commercial graft polymers, Impra® ePTFE (expanded polytetrafluoroethylene), which has been shown to have a low inflammatory effect in vivo, and Hemaschield®, a polyester-based graft material which is known to be highly inflammatory (D. L. Salzmann, et al., *Cardiovascular Pathology*, 1999, 8(2):63-71) was carried out. The result of the comparison, which is discussed in greater detail in Example 1, was that both the PEA-TEMPO and PEA-BZ discs elicited inflammatory responses that were equal to or less than that exhibited by the Impra® disc.

Figure 3:
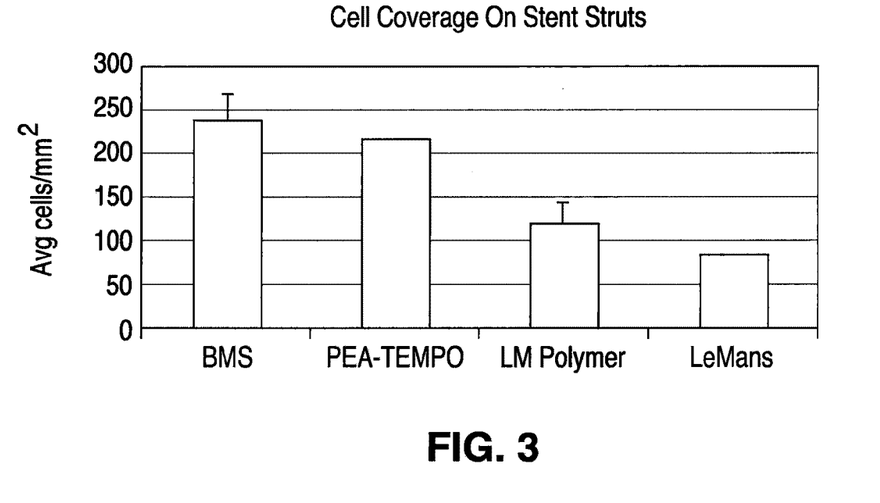
FIG. 3 graphically depicts endothelial cell coverage of a PEA-coated stent, a BMS and a Solef® (poly(vinylidene fluoride-co-hexafluoropropylene)-coated stent.

In addition, a comparison of the neovascularization kinetics of a stent coated with PEA-TEMPO was compared to that of a bare metal stent (BMS) and a poly(vinylidene fluoride-co-hexafluoropropylene) (SOLEF®) coated stent (Example 2) when the stents were implanted in a bioengineered vessel. The PEA-TEMPO-coated stent exhibited endothelial coverage only a little lower than that exhibited by the BMS and substantially greater than that exhibited by the SOLEF® stent.

Based on the above results, together with the fact that the poly(ester-amide) polymers of this invention are quite biocompatible, it is expected that coating implantable medical devices with a topcoat of a poly(ester-amide) herein should have a substantial beneficial effect on healing in the vicinity of the implanted device and thereby reduce the occurrence of problems associated with slow healing such as late-stage thrombosis. This should be particularly valuable with regard to drug eluting stents (DESs), which were initially introduced to counter the high rate of restenosis among recipients of BMSs. That is, while overcoming some of the shortfalls of percutaneous coronary angioplasty (PTCA), such as elastic recoil of the arterial wall resulting in dynamic re-narrowing of the vessel, BMSs were found to still be susceptible to restenosis, albeit at a substantially lower rate than unstented PTCAs (15-20% in stented patients versus 30-50% in previous unstented PTCAs). In 2002 the first DESs designed to address BMS restenosis were introduced. The stents were engineered to slowly release a cytostatic drug in the vicinity of the stent thereby slowing or preventing cell growth and resultant restenosis. DESs have reduced the incidence of restenosis to 5-7%. Since that time other drugs have been proposed for use with DESs, both to further improve the clinical results of stenting and to effect localized delivery of drugs to target sites in a patient's body to overcome problems with the drugs such as toxicity, bioavailability, solubility, etc. Thus, therapeutic agents with anti-proliferative, anti-inflammatory, antineoplastic, antiplatelet, anti-coagulant, antithrombonic, antimitotic, antibiotic, antiallergic and antioxidant properties have been proposed for use with DESs. Examples of suitable therapeutic agents include synthetic inorganic and organic compounds, proteins and peptides, polysaccharides and other sugars, lipids, DNA and RNA nucleic acid sequences, antisense oligonucleotides, antibodies, receptor ligands, enzymes, adhesion peptides, blood clot agents such as streptokinase and tissue plasminogen activator, antigens, hormones, growth factors, ribozymes, retroviral vectors, antiproliferative agents such as rapamycin (sirolimus), 40-O-(2-hydroxyethyl)rapamycin (everolimus), 40-O-(3-hydroxypropyl)rapamycin, 40-O-(2-hydroxyethyoxy)ethylrapamycin, 40-O-tetrazolylrapamycin, 40-epi(N1-tetrazolyl)rapamycin (zotarolimus, ABT-578), paclitaxel, docetaxel, methotrexate, azathioprine, vincristine, vinblastine, fluorouracil, doxorubicin hydrochloride, mitomycin, antiplatelet compounds, anticoagulants, antifibrin, antithrombins such as sodium heparin, low molecular weight heparins, heparinoids, hirudin, argatroban, forskolin, vapiprost, prostacyclin, prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä, calcium channel blockers such as nifedipine, colchicine, fibroblast growth factor (FGF) antagonists, fish oil (omega 3-fatty acid), histamine antagonists, lovastatin, monoclonal antibodies, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic, estradiol, anticancer agents, dietary supplements such as vitamins, anti-inflammatory agents such as aspirin, tacrolimus, dexamethasone and clobetasol, cytostatic substances such as angiopeptin, angiotensin converting enzyme inhibitors such as captopril, cilazapril or lisinopril, antiallergic agents is permirolast potassium, alpha-interferon, bioactive RGD, and genetically engineered epithelial cells. Other therapeutic agents which are currently available or that may be developed in the future for use with DESs may likewise be used and all are within the scope of this invention.

With regard to the present invention, everolimus, an immunosuppressive macrolide antibiotic, is a presently preferred therapeutic agent for use with an implantable medical device of this invention.

While a poly(ester-amide) of this invention may be incorporated into any of, any combination of, or all of the layers disposed over an implantable medical device of this invention, it is presently preferred that the poly(ester-amide) be included in at least the outermost layer coated on the device.

As used herein, "outermost layer" simply refers to that layer of material disposed over an implantable medical device of this invention that is in contact with bodily fluids and/or tissues of the patient in whom the device is implanted. The outermost layer is preferably at present a separate topcoat layer as described elsewhere herein but it may be a rate-controlling layer, if a topcoat layer is not opted, or even a drug reservoir layer if neither the topcoat layer nor the rate-controlling layer is opted.

Thus, it is an aspect of this invention that a poly(ester-amide) topcoat can be applied directly to the surface of a BMS. The healing characteristics of the poly(ester-amide) coating alone is expected to have a salutary effect on restenosis even without added therapeutic agent.

It is also an aspect of this invention, however, to include the poly(ester-amide) in a drug reservoir layer with no further layers being applied. This may be the case if the release profile of the therapeutic agent is not deleteriously affected by the inclusion of the poly(ester-amide) in that layer. Techniques for determining if the release profile of a particular therapeutic agent is acceptable for a particular application is well within the knowledge of those skilled in the art and need not be further described herein.

It is presently preferred, however, that an implantable medical device of this Invention comprises at least a topcoat layer and that the topcoat layer comprise a poly(ester-amide) of this invention.

As noted, there may be layers disposed between the poly (ester-amide) topcoat and the device body. A common additional layer would be a primer as described above. A primer may be used if it is found that the material of which the device body is constructed does not adhere well to the selected poly(ester-amide). While many primer polymers and polymer blends are known in the art and any of them can be used with the devices and methods herein, a currently preferred class of primers is the acrylate polymers, copolymers and blends thereof. Preferable at present, poly(n-butyl methacrylate) is a preferred primer for use with the devices and methods of this invention.

In lieu of or in addition to a primer, a drug reservoir layer may also be included between the device body and the topcoat layer. A separate drug reservoir layer may be required if, without limitation, if is found that a desired therapeutic agent is not sufficiently compatible with the poly(ester-amide) to provide the desired agent concentration, if the desired release profile cannot be achieved, etc. The drug reservoir layer may comprise simply the drug alone, that is, neat. This can be accomplished by dissolving the drug in a suitable solvent, applying the solution atop a primer that has been coated on the device body, and removing the solvent leaving a layer of drug alone. The poly(ester-amide) topcoat may then be applied directly over the neat drug layer.

In the alternative, the therapeutic agent may be formulated with a polymer or polymer blend. Thus, therapeutic agent and polymer can be dissolved in a suitable solvent or the polymer can be dissolved and the therapeutic agent evenly dispersed in the polymer solution. The solution or mixture can then be applied to either the device body or over a primer layer. When the solvent is removed the drug is left suspended in polymer. The polymer or polymer blend is selected to provide the desired release profile. At times, however, a polymer that is compatible with the drug may not afford the desired release profile or a polymer that can provide the desired profile is not sufficiently compatible with the drug. This situation may be ameliorated by the inclusion of a rate-controlling layer over the drug reservoir layer.

A rate-controlling layer, as the name implied, consists of a polymer through which the drug has been shown to elute at the desired rate when the correct polymer, correct polymer concentration and correct layer thickness is used. Again, these parameters are readily determinable by those skilled in the art.

While, as noted above, an implantable medical device of this invention may encompass a large array of devices, a presently preferred device is a coronary stent and a presently preferred therapeutic agent for use with the stent is everolimus. It is further presently preferred that an implantable medical device herein comprise a primer applied directly to the device body and then a drug reservoir layer comprising poly(ethylidene fluoride) and everolimus, applied over the primer layer. A pro-healing poly(ester-amide) topcoat is then applied over the drug reservoir layer. A rate-controlling layer may be present but is not necessarily so in that it has been determined (data not shown) that certain formulations of poly(vinylidene fluoride-co-hexafluoropropylene)/everolimus drug reservoir layers exhibit desirable release profiles. A more detailed description of this aspect of this invention is provided in Example 3.

On the other hand, if release profiles not achievable using poly(ethylidene fluoride) or poly(ester-amide) in the drug reservoir layer or poly(ester-amide) as a combination rate-controlling/topcoat are desired, a separate rate-controlling layer may be used. Once again, different rate-controlling polymers or polymer blends useful with different therapeutic agents are known in the art and all are within the scope of this invention so long as a poly(ester-amide) topcoat layer is applied as the outermost layer on the implantable device.

As noted above, everolimus is a presently preferred therapeutic agent for use herein. As it turns out, the presently preferred pro-healing poly(ester-amide)s, PEA-TEMPO and PEA-BZ, are quite permeable to everolimus and cannot alone provide achieve desirable sustained-release profiles. If the drug reservoir layer likewise cannot provide completely the desired profile, a rate-controlling layer may be disposed atop the drug reservoir layer can be employed. Presently preferred polymers useful for establishing desired everolimus release profiles are poly(L-lactide), poly(D-lactide), poly(D,L-lactide), poly(meso-lactide), poly(L-lactide-co-glycolide), poly (D-lactide-co-glycolide), poly(D,L-lactide-co-glycolide), poly(meso-lactide-co-glycolide) or any combination thereof. Most preferred at present in poly(D,L-lactide). A concrete, but in no way limiting, example of an implantable medical device that follows the above protocol would be:

a 12 mm Vision® stent;
168 μg total weight of a 1:2 wt/wt mixture of everolimus/PEA-TEMPO drug reservoir layer disposed over the stent;
40 μg of poly(D,L-lactide) disposed as a rate-controlling layer over the drug reservoir layer; and,
a 75 μg of PEA-TEMPO as a pro-healing topcoat layer.
Another, likewise non-limiting, example would be:
100 μg of PEA-TEMPO applied to a 12 mm Vision® stent as a primer layer;
56 μg neat everolimus applied atop the primer layer as the drug reservoir layer;
40 μg of poly(D,L-lactide) applied atop the neat everolimus layer as a rate-controlling layer; and,
75 μg of PEA-TEMPO as a topcoat pro-healing layer.

As noted previously, a separate rate-controlling layer may not be necessary if the therapeutic agent is sufficiently compatible with an effective rate-controlling polymer to be included in the same layer with it. Such is the case with everolimus and poly(D,L-lactide), Thus yet another non-limiting construct of this invention is envisioned to comprise:

100 μg poly(D,L-lactide) coated on a 12 mm Vision® stent;
112 μg total weight of a 1:1 everolimus/poly(D,L-lactide) drug reservoir layer/rate-controlling layer; and,
150 μg of PEA-TEMPO as a pro-healing topcoat.

EXAMPLES

Example 1

The inflammatory response of PEA-TEMPO and PEA-BZ was evaluated using a rat epicardial model. Hemashield® graft material was used as a highly inflammatory control and Impra® ePTFE graft material was used as a minimally inflammatory control. Four millimeter diameter 300 μm thick discs of each polymer were implanted onto rat epicardial surface and the inflammation level was measured at 14 days and at 30 days. The control discs exhibited inflammatory and cellular responses typical of those materials. Both PEA-TEMPO and PEA-BZ exhibited cellular and inflammatory responses that were equal to or less than that of the Impra® disc. The results are shown graphically in FIGS. 1 and 2.

Example 2

The re-endothelialization kinetics of PEA-TEMPO coated on a stent were compared to those of a bare metal stent (BMS) and a stent coated with Solef® (poly(vinylidene fluoride-co-hexafluoropropylene). Medium Vision® 4.0×18 mm stents were used bare, coated with 1494 μg of PEA-TEMPO or coated with 767 μg of Solef®. The stents were implanted in a bioengineered vessel and evaluated after 7 days. The stented vessels were stained with bisbenzimide (BBI), cut in half longitudinally and imaged with a 10× objective. The images were imported into MetaMorph® software for analysis. In each image, the stent tine area was traced and quantified. The cells covering the stent tine were then counted manually. Tine area was converted into $mm^2$ using a conversion factor determined with a standard stage microscope. The number of cells/$mm^2$ was calculated for each image and averaged for each vessel. PEA-TEMPO-coated stents were found to have endothelial cell coverage similar to the BMS and substantially greater than the Solef®-coated stents. The results are shown graphically in FIG. 3.

Example 3

Figure 4:
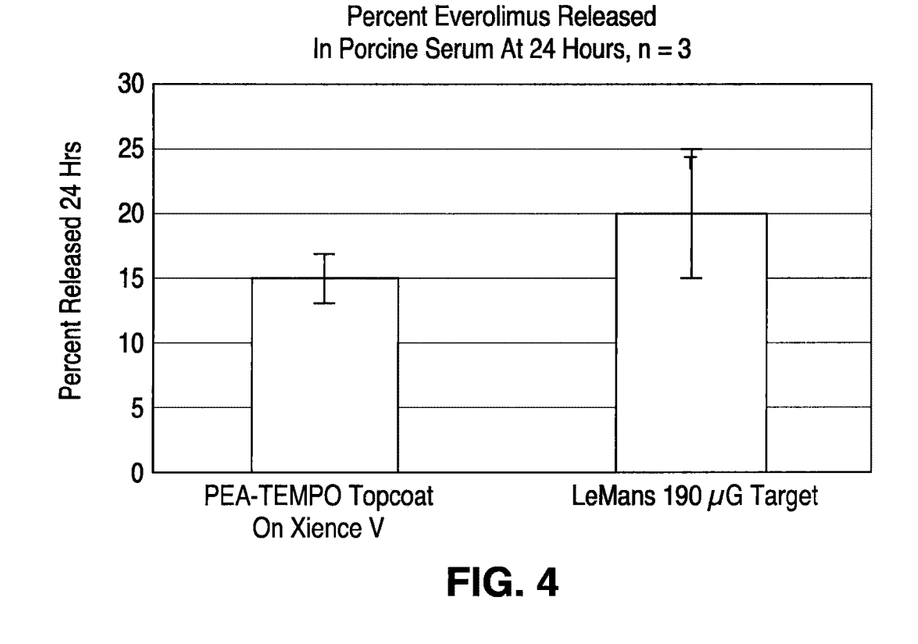
FIG. 4 graphically depicts the percentage everolimus released by a stent without a topcoat, which establishes a target release rate, compared with a stent having a topcoat of a poly(ester-amide) of this invention.

A poly(ester-amide) topcoat was applied over a small 18 mm stent having a poly(n-butyl methacrylate) primer and a drug reservoir layer of poly(vinylidene fluoride-co-hexafluoropropylene) containing 190 μg of everolimus. The poly(ester-amide) used was PEA-TEMPO and 89 μg were applied to the stent over the drug reservoir layer. The release rate target of the stent absent the topcoat is shown on the right in FIG. 4. The release rate obtained with the PEA-TEMPO is shown on the left. As can be seen, the permissible standard deviations overlap, indicating that the PEA-TEMPO topcoat did not detrimentally interfere with the target release rate.

Example 4

The effect of a poly(ester-amide) topcoat layer on the mechanical integrity of the stent of Example 3 was examined. A small 18 mm Vision® stent was coated with a poly(n-butyl methacrylate) primer and a drug reservoir layer of poly(vinylidene fluoride-co-hexafluoropropylene) containing 190 μg of everolimus. Over the drug reservoir layer, 89 μg of PEA-TEMPO was spray-coated from a 2 wt % solids absolute ethanol solution resulting in an approximately 0.92 μm thick coating of the poly(ester-amide). The coating was then examined post-wet expansion from an overall, an outside diameter and an inside diameter perspective. It was found that the PEA-TEMPO coating did not introduce any observable coating integrity failures on wet expansion.

What is claimed:
1. An implantable medical device, comprising:
a device body;
an optional primer layer disposed over the device body;
a drug reservoir layer disposed over the device body or the primer layer, if opted, wherein the drug reservoir layer comprises one or more therapeutic agents;
an optional rate-controlling layer disposed over at least a portion of the drug reservoir layer, if opted; and,
an optional top-coat layer disposed as an outermost layer over the device body, the primer layer, if opted, the drug reservoir layer, if opted, or the rate-limiting layer, if opted, wherein:
at least one of the layers comprises a poly(ester-amide) having the formula:

wherein:
m is an integer from 1 to about 200;
p is an integer from 1 to about 200;
n is an integer from 1 to about 200;
r is an integer from 1 to about 3000;
$M_w$ is from about 10,000 Da to about 1,000,000 Da;
s is a number from 0 to 1, inclusive;
t is a number from 0 to 1, inclusive;
v is a number from 0 to 1, inclusive; wherein:

$s+t+v=1$;

X has the chemical structure:

Y has the chemical structure:

Z has the chemical structure:

, wherein:

$R_1$, $R_{1'}$ and $R_4$ are independently selected from the group consisting of (1C-12C)alkyl and (2C-12C)alkenyl;

$R_2$, $R_{2'}$, $R_{2''}$ and $R_{2'''}$ are independently selected from the group consisting of hydrogen and (1C-4C)alkyl, wherein:

the alkyl group is optionally substituted with a moiety selected from the group consisting of —OH, —O(1C-4C)alkyl, —SH, —S(1C-4C)alkyl, —SeH, —$COR_6$, —$NHC(NH)NH_2$, imidazol-2-yl, imidazole-5-yl, indol-3-yl, phenyl, 4-hydroxyphenyl and 4-[(1C-4C)alkylO]phenyl, wherein:

$R_6$ is selected from the group consisting of —OH, —O(1C-4C)alkyl, —$NH_2$, —NH(1C-4C)alkyl, —N(1C-4C)alkyl$_1$(1C-4C)alkyl$_2$, a stable nitroxide, —$O(CH_2)_2OP(=O)(O^-)OCH_2CH_2N^+(CH_3)_3$, —$O(CH_2CH_2O)_qCH_2CH_2OR_7$ and

;

where:
$R_7$ is selected from the group consisting of hydrogen, (1C-4C)alkyl, —$C(O)CH=CH_2$, —$C(O)C(CH_3)=CH_2$ and —$O(CH_2)_2OP(=O)(O^-)OCH_2CH_2N^+(CH_3)_3$; or one or more of $R_2$, $R_{2'}$, $R_{2''}$ and $R_{2'''}$ may form a bridge between the carbon to which it is attached and the adjacent nitrogen, the bridge comprising —$CH_2CH_2CH_2$—;

$R_3$ is selected from the group consisting of (1C-12C)alkyl and (2C-12C)alkenyl, (3C-8C)cycloalkyl, (3C-8C)bicycloalkyl and —$(CH_2CH_2O)_qCH_2CH_2$—;

$R_5$ is selected from the group consisting of —$CH(COR_6)CH_2S$—, —$CH(COR_6)CH_2O$—, —$CH(COR_6)(CH_2)_4NH$—, —$(CH_2)_4CH(COR_6)NH$—, —$CH(COR_6)CH(CH_3)O$—, and ; and, q is an integer from 1 to 600, inclusive.

2. The implantable medical device of claim 1, wherein $M_w$ is from about 20,000 Da to about 500,000 Da.

3. The implantable medical device of claim 1, wherein at least an outermost layer comprises the poly(ester-amide).

4. The implantable medical device of claim 3, wherein the outermost layer is a topcoat layer.

5. The implantable medical device of claim 1, wherein:
$R_1$ is selected from the group consisting of —$(CH_2)_4$—, —$(CH_2)_8$—, and —$CH_2CH=CHCH_2$—; and,
$R_{1'}$ and $R_4$ are selected from the group consisting of —$(CH_2)_4$— and —$(CH_2)_8$—.

6. The implantable medical device of claim 5, wherein $R_2$ is —$CH_2CH(CH_3)_2$.

7. The implantable medical device of claim 6, wherein: $R_3$ is —$(CH_2)_6$—; and, $R_{3'}$ is

.

8. The implantable medical device of claim 7, wherein $R_5$ is —$(CH_2)_4CH(COR_6)NH$—, wherein:
$R_6$ is selected from the group consisting of —$O(CH_2)_2OP(=O)(O^-)OCH_2CH_2N^+(CH_3)_3$ and —$O(CH_2CH_2O)_qCH_2CH_2OR_7$, wherein:
$R_7$ is selected from the group consisting of hydrogen, (1C-4C)alkyl, —$C(O)CH=CH_2$ and —$C(O)C(CH_3)=CH_2$.

9. The implantable medical device of claim 1, wherein $R_1$ and $R_4$ are independently selected from the group consisting of —$(CH_2)_4$— and —$(CH_2)_8$—.

10. The implantable medical device of claim 9, wherein $R_2$ and $R_{2'}$ are independently selected from the group consisting of —$CH_3$, —$CH_2CH_2NHC(NH)NH_2$, —$CH_2CONH_2$, —$CH_2COOH$, —$CH_2SH$, —$CH_2CH_2COOH$, —$CH_2CH_2CONH_2$, —$CH_2NH_2$,

—$CH(CH_3)CH_2CH_3$, —$CH_2CH(CH_3)_2$, —$(CH_2)_4NH_2$, —$(CH_2)_2SCH_3$,

—$CH_2OH$, —$CH(CH_3)OH$,

,

,

CH(CH₃)₂ and —CH₂CH₂CH₂—, wherein the second carbon is covalently bonded to the nitrogen adjacent to the carbon to which $R_2$ is bonded.

11. The implantable medical device of claim 10, wherein $R_3$ is selected from the group consisting of —(CH₂)₃—, —(CH₂)₆— and —(CH₂CH₂O)$_q$CH₂CH₂—, wherein q is an integer from 1 to 10, inclusive.

12. The implantable medical device of claim 11, wherein $R_5$ is —(CH₂)₄CH(COR₆)NH—, wherein:
  $R_6$ is selected from the group consisting of a stable nitroxide,

,

—O(CH₂)₂OP(=O)(O⁻)OCH₂CH₂N⁺(CH₃)₃ and —O(CH₂CH₂O)$_q$CH₂CH₂OR₇, wherein:
  $R_7$ is selected from the group consisting of hydrogen, (1C-4C)alkyl, —C(O)CH=CH₂ and —C(O)C(CH₃)=CH₂.

13. The implantable medical device of claim 11, wherein $R_2$ and $R_{2'}$ are the same.

14. The implantable medical device of claim 13, wherein $R_2$ and $R_{2'}$ are —CH₂CH(CH₃)₂.

15. The implantable medical device of claim 1, wherein the stable nitroxide is selected from the group consisting of

16. The implantable medical device of claim 15, wherein the stable nitroxide is

17. The implantable medical device of claim 14, wherein $R_6$ is

.

18. The implantable medical device of claim 1, wherein $R_2$ and $R_{2'}$ are selected from the group consisting of —CH₃, —H₂CH₂NHC(NH)NH₂, —CH₂CONH₂, —CH₂COOH, —CH₂SH, —CH₂CH₂COOH, —CH₂CH₂CONH₂, —CH₂NH₂,

,

—CH(CH₃)CH₂CH₃, —CH₂CH(CH₃)₂, —(CH₂)₄NH₂, (CH₂)₂SCH₃,

,

CH₂OH, —CH(CH₃)OH,

,

CH(CH₃)₂ and —CH₂CH₂CH₂—, wherein the second carbon is covalently bonded to the nitrogen adjacent to the carbon to which $R_2$ is bonded.

19. The implantable medical device of claim 18, wherein $R_1$ is selected from the group consisting of —$(CH_2)_4$—, —$(CH_2)_8$— and —$CH_2CH$=$CHCH_2$—.

20. The implantable medical device of claim 19, wherein $R_2$ and $R_{2'}$ are the same.

21. The implantable medical device of claim 20, wherein $R_2$ and $R_{2'}$ are $CH_2CH(CH_3)_2$.

22. The implantable medical device of claim 21, wherein $R_3$ is selected from the group consisting of (3C-8C) alkyl, —$(CH_2CH_2O)_qCH_2CH_2$—, wherein q is an integer from 1 to 10, inclusive, 23. The implantable medical device of claim 22, wherein q is 2.

24. The implantable medical device of claim 21, wherein $R_3$ is selected from the group consisting of —$(CH_2)_3$— and —$(CH_2)_6$—.

25. The implantable medical device of claim 21, wherein $R_3$ is

26. The implantable medical device of claim 24, wherein $R_2$ and $R_{2'}$ are benzyl.

27. The implantable medical device of claim 1, comprising a drug reservoir layer and a rate-controlling layer, wherein the rate-controlling layer comprises a polymer selected from the group consisting of poly(L-lactide), poly(D-lactide), poly(D,L-lactide), poly(meso-lactide), poly(L-lactide-co-glycolide), poly(D-lactide-co-glycolide), poly(D,L-lactide-co-glycolide), poly(meso-lactide-co-glycolide) and an combination thereof.

28. The implantable medical device of claim 27, wherein the rate-controlling layer comprises poly(D,L-lactide).

29. The implantable medical device of claim 1, comprising a drug reservoir layer, wherein the drug reservoir layer comprises one or more drugs disposed neat over the primer layer.

30. The implantable medical device of claim 1, comprising a drug reservoir layer, wherein the drug reservoir layer comprises one or more polymers.

31. The implantable medical device of claim 30, wherein the drug is everolimus.

32. The implantable medical device of claim 31, wherein the drug reservoir layer polymer is selected from the group consisting of poly(vinylidene fluoride) and poly(vinylidene fluoride-co-hexafluoropropylene).

33. The implantable medical device of claim 32, further comprising a primer layer, wherein the primer layer comprises poly(n-butyl methacrylate).

34. The implantable medical device of claim 33, wherein the device is a stent.

35. The implantable medical device of claim 1, wherein one or more of $R_2$, $R_{2'}$, $R_{2''}$, $R_{2'''}$ and $R_5$ comprises a pendant —$COR_6$ group wherein each $R_6$ is independently selected from the group consisting of a stable nitroxide entity, benzylO—, —$O(CH_2)_2OP$(=$O$)($O$)$CH_2CH_2N^+(CH_3)_3$ and —$O(CH_2CH_2O)_qCH_2CH_2OR_7$.

36. The implantable medical device of claim 35, wherein at least an outermost layer comprises the poly(ester-amide).

37. The implantable medical device of claim 36, wherein the outermost layer is a topcoat layer.

38. The implantable medical device of claim 35, wherein the stable nitroxide is selected from the group consisting of 39. The implantable medical device of claim 35, wherein q is 1-10, inclusive.

40. The implantable medical device of claim 35, wherein q is 300-600, inclusive.

41. The implantable medical device of claim 35, wherein $R_6$ is —$O(CH_2)_2OP$(=$O$)($O$)$CH_2CH_2N^+(CH_3)_3$.

42. The implantable medical device of claim 1, wherein the device is a stent.

* * * * *